(12) United States Patent
Chen et al.

(10) Patent No.: US 12,089,577 B2
(45) Date of Patent: Sep. 17, 2024

(54) INSECT-RICE SYMBIOTIC COMPREHENSIVE PLANTING AND BREEDING METHOD MAINLY BASED ON TYLORRHYNCHUS PROLIFERATION

(71) Applicants: YANGJIANG POLYTECHNIC, Guangdong (CN); GUANGDONG YANGHAI AGRICULTURE DEVELOPMENT CO., LTD, Guangdong (CN)

(72) Inventors: Xinghan Chen, Yangjiang (CN); Qiyong Liang, Yangjiang (CN); Wei Yang, Yangjiang (CN); Yuanyuan Si, Yangjiang (CN); Bin Fan, Yangjiang (CN); Ruiwen Xu, Yangjiang (CN); Xiaoming Tan, Yangjiang (CN)

(73) Assignee: YANGJIANG POLYTECHNIC, Yangjiang (CN)

( * ) Notice: Subject to any disclaimer, the term of this patent is extended or adjusted under 35 U.S.C. 154(b) by 268 days.

(21) Appl. No.: 17/639,422

(22) PCT Filed: Dec. 20, 2021

(86) PCT No.: PCT/CN2021/139689
§ 371 (c)(1),
(2) Date: Mar. 1, 2022

(87) PCT Pub. No.: WO2022/156458
PCT Pub. Date: Jul. 28, 2022

(65) Prior Publication Data
US 2023/0345920 A1 Nov. 2, 2023

(30) Foreign Application Priority Data

Jan. 22, 2021 (CN) .......................... 202110089550.5

(51) Int. Cl.
*A01K 67/033* (2006.01)
*A01G 22/22* (2018.01)

(52) U.S. Cl.
CPC ............ *A01K 67/033* (2013.01); *A01G 22/22* (2018.02)

(58) Field of Classification Search
CPC .............................. A01K 67/033; A01G 22/22
See application file for complete search history.

(56) References Cited

U.S. PATENT DOCUMENTS

2003/0089652 A1* 5/2003 Matsui ...................... C02F 1/00
210/170.03
2004/0159288 A1* 8/2004 Olive ................. A01K 67/0332
119/6.7
(Continued)

FOREIGN PATENT DOCUMENTS

CN 1929735 B * 6/2011 ............. A01N 25/02
CN 104782582 A * 7/2015 ........... A01K 67/033
(Continued)

OTHER PUBLICATIONS

"Management of the exploitation of the lugworm *Arenicola marina* and the ragworm *Nereis virens* (Polychaeta) in conservation areas" Wiley Online Library <https://onlinelibrary.wiley.com/doi/10.1002/aqc.3270030102> (Year: 1993).*
(Continued)

*Primary Examiner* — Morgan T Jordan
(74) *Attorney, Agent, or Firm* — Dorsey & Whitney LLP

(57) ABSTRACT

A Tylorrhynchus-rice symbiotic comprehensive planting and breeding method mainly based on tylorrhynchus proliferation is provided. The planting method includes: paddy field selection; field layout, wherein an inlet pipe and a drainage pipe controlled by an inlet control assembly and a drainage control assembly, respectively, are provided in the paddy field, and said inlet pipe is provided with an inter-
(Continued)

cepting net for intercepting pest predators; soil preparation and fertilization; stocking of Tylorrhynchus and seedlings; management of Tylorrhynchus proliferation; rice planting; field management; water level control; rice harvesting; Tylorrhynchus capturing. A comprehensive breeding mode of symbiosis between Tylorrhynchuss and rice is provided. By first proliferating the Tylorrhynchuss in the rice field and then planting rice, it can simulate the growth environment of the Tylorrhynchuss in the field to the greatest extent, and give full play to the mutually beneficial symbiotic relationship between Tylorrhynchuss and rice.

7 Claims, 7 Drawing Sheets

(56) References Cited

U.S. PATENT DOCUMENTS

| | | | |
|---|---|---|---|
| 2011/0296756 A1* | 12/2011 | Zhang | A01K 39/00 119/6.5 |
| 2012/0029709 A1* | 2/2012 | Safreno | A01G 25/16 700/284 |
| 2022/0009796 A1* | 1/2022 | Canuto | C02F 1/283 |

FOREIGN PATENT DOCUMENTS

| | | | | |
|---|---|---|---|---|
| CN | 104855781 A | * | 8/2015 | |
| CN | 106665504 A | * | 5/2017 | ........... A01C 21/005 |
| CN | 111699935 A | * | 9/2020 | |
| CN | 111771842 A | * | 10/2020 | |
| CN | 112088717 A | * | 12/2020 | ............ A01G 18/00 |

OTHER PUBLICATIONS

"Effects of earthworms on soil properties and rice production in the rainfed paddy fields of Northeast Thailand" Choosai et al. Applied Soil Ecology (Year: 2010).*
Merged translation of CN_1929735 (Year: 2011).*
Merged translation of CN_104782582 (Year: 2015).*
Merged translation of CN_104855781 (Year: 2015).*
Ragworm Paddy Project, Rueco (Year: 2016).*
Merged translation of CN_106665504 (Year: 2017).*
"Palolo worm" The Editors of Encyclopedia Brittanica <http://web.archive.org/web/20180917130254/https://www.britannica.com/animal/palolo-worm> (Year: 2018).*
Merged translation of CN_111699935 (Year: 2020).*
Merged translation of CN_111771842 (Year: 2020).*
Merged translation of CN_112088717 (Year: 2020).*
"Tylorrhynchus heterochetus" Wikipedia, <https://en.wikipedia.org/wiki/Tylorrhynchus_heterochetus> (Year: 2023).*

* cited by examiner

(12) United States Patent

INSECT-RICE SYMBIOTIC COMPREHENSIVE PLANTING AND BREEDING METHOD MAINLY BASED ON TYLORRHYNCHUS PROLIFERATION

CROSS-REFERENCE TO RELATED APPLICATION

This application is a U.S. National Stage of PCT International Application No. PCT/CN2021/139689 filed on Dec. 20, 2021, which claims the priority to Chinese Patent Application No. 202110089550.5 filed on Jan. 22, 2021, and having a title "A Tylorrhynchus-rice symbiotic integrated planting and breeding method mainly based on tylorrhynchus proliferation", the disclosure of which is incorporated by reference herein in its entirety as part of the present application.

TECHNICAL FIELD

The present disclosure belongs to the technical field of agricultural breeding, and specifically relates to a Tylorrhynchus-rice symbiotic integrated planting and breeding method mainly based on tylorrhynchus proliferation.

BACKGROUND

Tylorrhynchus, the scientific name Tylorrhynchus heterochaetus, like to inhabit rice fields or shallow silt sandy soils in the confluence of salt and fresh water. It is omnivorous and feeds on unicellular algae and animal and plant carcasses. It can effectively use the nutrients in the mud. The worms are delicious, rich in unsaturated fatty acids, hydroxyl acid, iodic acid, fibrinolytic acid, collagenase, calcium, phosphorus and other macro elements and iron, zinc, selenium and other trace elements. They are rich in nutrition and good for medicine and food. It is a popular food and diet health care product in the southeast coast, Hong Kong, Macao of our country and Southeast Asian countries. It has great development and utilization value and has a broad market prospect. At present, the Tylorrhynchus breeding industry mainly relies on natural seedlings for artificial beach protection. This process is extremely vulnerable to uncontrollable factors such as nutrient deficiency, salt tide invasion, and deterioration of water quality; coupled with outstanding problems such as environmental pollution, the number of Tylorrhynchus has gradually decreased in recent years. These reasons lead to unstable production of Tylorrhynchus, with an average annual yield of only 10-50 Catties per Chinese acre, and low breeding efficiency. Therefore, it is necessary to innovate the breeding model of Tylorrhynchus.

Integrated rice cultivation is a production method that organically integrates planting and breeding in the same ecological environment. This model can make full use of the limited water ecological environment and space of the rice field, maximize the use of resources, reduce waste and pollution, and increase the output rate; it is beneficial to increase the economic output value and the income of farmers, and realize the green, safe production and sustainable development of agriculture. It is of great significance for ensuring the quality of agricultural products and improving the level of food safety, and has been widely recognized by the country and all sectors of society. At present, rice cultivation is most closely related to aquaculture. The integrated rice-fishing cultivation model mostly combines rice planting with fish, shrimp, crab, turtle and other aquatic animals. However, this type of production often requires manual feeding of a large amount of feed and fine aquaculture management. The material and manpower inputs are relatively high, which cannot effectively improve the utilization rate of rice fields and the comprehensive production benefits, and it is difficult to carry out large-scale promotion.

SUMMARY

The purpose of this publication is to address the unstable yield and low efficiency of traditional grass and Tylorrhynchus breeding models, as well as the current comprehensive rice-fishing planting and breeding models that require fine aquaculture management and high material and manpower inputs, low rice field utilization and production benefits, difficult to popularize and other disadvantages, and a new Tylorrhynchus-rice symbiotic comprehensive planting and breeding method mainly based on Tylorrhynchus proliferation is proposed.

The Tylorrhynchus-rice symbiotic comprehensive planting and breeding method mainly based on Tylorrhynchus proliferation makes full use of the natural symbiotic relationship between the Tylorrhynchuss and rice. The larvae of the Tylorrhynchuss are first stocked in the paddy field, and then the rice is planted for the comprehensive cultivation of Tylorrhynchuss and rice. When the Tylorrhynchuss are proliferated and cultivated, the wild growth environment of the Tylorrhynchus is simulated to the greatest extent, and the most suitable habitat is provided for the growth of the Tylorrhynchus. The rotten rice roots and stems and leaves can provide nutrients for the Tylorrhynchus, and the rice roots and hollow stems can transport oxygen for the Tylorrhynchus; the Tylorrhynchus feed on the microorganisms and organic debris in the soil, which can reduce the occurrence of rice diseases. The Tylorrhynchus drilling holes can dredge the soil, and its manure is a high-quality organic fertilizer. Ultimately increase the survival rate of Tylorrhynchus, increase rice output, improve rice quality, and significantly increase the economic benefits of rice farming.

The technical scheme employed by the present disclosure:

A Tylorrhynchus-rice symbiotic comprehensive planting and breeding method mainly based on Tylorrhynchus proliferation, wherein the planting and breeding method comprises the following steps:

Step S1: paddy field selection;

External source water of the paddy field is sufficient, water quality is good, irrigation and drainage is convenient, and there is no industrial sewage pollution;

Step S2: field layout;

Step S3: soil preparation and fertilization;

The paddy field should be applied with sufficient base fertilizer, and an amount of fertilizer should be controlled at 1000-2000 kg/Chinese acre according to the fertility of the land, evenly spread into the field, irrigate and prepare the land;

Step S4: stocking of Tylorrhynchus;

From February to April or from July to August every year, after the rice field is leveled and the base fertilizer is applied, release Tylorrhynchus 7 to 15 days before transplanting;

Step S5: management of Tylorrhynchus proliferation;

After the feed is crushed and fermented, fully mix with 10 times the weight of the dry rice stalk powder and feed evenly; once a week, a feeding amount is 3% of the weight of the Tylorrhynchus, reduce the feeding amount on cloudy days and low air pressure, not to feed when the water temperature is higher than 35° C. or lower than 15° C.;

Step S6: rice planting;

Choose rice varieties with strong fertility tolerance, lodging resistance, strong disease resistance, moderate growth period, and good quality, and mechanical harrowing the field more than 2 times to make the mud floating and rotten, the field surface is fully leveled, and the height difference of the field surface is not more than 3 cm; use mechanical transplanting or throwing seedlings, planting 100,000 basic seedlings per Chinese acre;

Step S7: field management;

Fertilization is mainly based on basic fertilizer, supplemented by topdressing, mainly organic fertilizer, supplemented by chemical fertilizers, topdressing is little amount and multiple times, select good quality cold commercial organic fertilizers, and the use of urea and other chemical fertilizers harmful to Tylorrhynchus is strictly prohibited; prevention should be primary control of diseases, pests and weeds in paddy field, comprehensive prevention and control, and reduce the amount of pesticide application; strictly control the safe use of pesticide concentration, spray the pesticide on the rice leaf, not into the water, and apply the pesticide in different areas, add water to the rice field to 15-20 cm before spraying, and change the water in time after spraying;

Step S8: water level controlling;
Step S9: rice harvesting;
Step S10: Tylorrhynchus capturing.

Preferably, the step S2 comprises: digging a ring-shaped ditch 3 along the inner side of the ridge around the paddy field and 0.5 to 1 meter away from the ridge, a ditch width 0.8-1 m, a depth 0.3-0.5 m; heightening, widening and tamping the ridge, the ridge height is 50-60 cm, the bottom width is 60-70 cm, the top width is 50-60 cm; on the side of the rice field an inlet channel 5 is built on the ridge to connect the inlet pipe to the paddy field, the drainage pipe 9 is built at the bottom of the ring-shaped ditch on the other side of the rice field, the inlet pipe and the drainage pipe are respectively provided with water inlet control assemblys and drainage control assemblys 10, and a plurality of grille nets 11 are arranged at the outlet of the inlet pipe 6 and the drainage hole of the drainage pipe 9.

Preferably, the water inlet of the water inlet pipe 6 is equipped with an interception net 8, and the side profile of the interception net 8 is "W"-shaped structure, the interception net 8 comprises a solid section 803 extending along the inner wall of the water inlet pipe 6, and the distal end of the solid section 803 is provided with a large grid evacuation area 802 and a small grid dense area 801 connected in series at intervals, the small grid dense area 801 distributed at the bending apex of the interception net 8, the proximal end of the solid section 803 is provided with an eversion part 804, and the eversion part 804 is attached to the side wall of the water inlet channel 5 and is fixedly connected by a screw.

Preferably, the water inlet control assembly 7 comprises an upper ring 701 and a lower ring 702 installed in the inner cavity of the water inlet pipe 6, the upper ring 701 is fixedly installed in the inner cavity of the water inlet pipe 6, the inner ring of the upper ring 701 is provided with evenly spaced connecting plates, the lower ring 702 is slidable along the inner cavity of the water inlet pipe 6, and the proximal end surface of the lower ring 702 is provided with a sealing plate intersecting the connecting plate 703, when the lower ring 702 moves up below the upper ring 701, the sealing plate 704 and the connecting plate 703 are spaced apart to form a solid plate to block the water in the water inlet channel 5 from passing through the water inlet pipe 6;

A push rod 705 is provided on the side wall of the lower ring 702, the free end of the push rod 705 extends from a guide hole 713 on the wall of the water inlet pipe 6 to the outside of the water inlet pipe 6, and the guide hole 713 is arranged between the upper ring 701 and the lower ring 702, the free end of the push rod 705 is movably connected with a movable rod 706, the end of the movable rod 706 is threadedly connected with an adjusting nut 709, the upper end and the lower end of the guide hole 713 are respectively provided with an upper clamping plate 707 and a lower clamping plate 708, the ends of the upper clamping plate 707 and the lower clamping plate 708 are both provided with mounting grooves recessed toward the wall of the water inlet pipe 6.

Preferably, guide grooves 710 are respectively provided on both sides of the guide hole 713, and there are a plurality of guide rods 711 between the two guide grooves 710, wherein the guide rod 711 located at each end of the guide groove 710 are fixedly connected with the guide groove 710, and a shielding cloth 712 is arranged under the guide rods 711, and when the shielding cloth 712 is unfolded, it closely adheres to the outer end of the guide hole 713.

Preferably, the inner diameter of the lower ring 702 is smaller than the inner diameter of the upper ring 701.

Preferably, the drainage control assembly 10 comprises a pipe cap 1001, and the pipe cap 1001 is sleeved on the drainage outlet of the drainage pipe 9, the pipe cap 1001 is provided with a drainage hole communicating with the inner cavity of the drainage pipe 9, and the outer wall of the pipe cap 1001 is provided with a shielding plate 1002 which is connected to the outer wall of the pipe cap 1001 through a fixing lock cap 1003, and the shielding plate 1002 is rotatable around a fixing lock cap 1003, the bottom of the outer wall of the shielding plate 1002 is provided with a protrusion 1004, the bottom of the outer wall of the pipe cap 1001 is provided with a fixing plate 1005 coaxial with the protrusion 1004, and the protrusion 1004 and the fixing plate 1005 are connected by a fixing rod 1006.

Preferably, wherein the lower end of the fixing rod 1006 is threadedly connected with an adjusting lock cap 1008, the upper end of the fixing rod 1006 is bent along the upper end surface of the protrusion 1004 to form a horizontal section, and an lower end surface of the horizontal section is provided with an arc-shaped block 1007, and the arc-shaped block 1007 is embeddable in the groove on the protrusion 1004, so as to realize the shielding plate 1002 to shield the drainage hole.

Preferably, the outer wall of the shielding plate 1002 is provided with a first fixing block 1009, and the outer wall of the pipe cap 1001 is provided with a second fixing block 1010, the first fixing block 1009 and the second fixing block 1010 are connected by a compression spring 1011.

Preferably, in the above step S10, the Tylorrhynchus capturing comprises: when the Tylorrhynchuss are sexually mature, dry the rice field for 1 to 2 days, in the dark night, water 20 to 30 cm, after a large number of sexually mature Tylorrhynchuss float, open the drainage pipe 9 and arrange a soft gauze net at the drain to catch the Tylorrhynchus, the captured Tylorrhynchus are placed in a container with holes, when the Tylorrhynchus are drilled out of the holes to separate them from the debris, then clean with clean water at 14° C.-18° C. for 2 to 3 times, and temporarily store at 13° C.-15° C.

Compared with the prior art, the beneficial effect of the present disclosure is that: the present disclosure employs the mode of symbiotic comprehensive planting and breeding method of Tylorrhynchus-rice, by first proliferating the Tylorrhynchus in the rice field, and then planting the rice, it simulates the Tylorrhynchus in the wild conditions to the greatest extent. The growth environment gives full play to the mutually beneficial symbiotic relationship between the Tylorrhynchus and the rice. The rotten rice roots, stems and leaves can provide food for the Tylorrhynchus, and the Tylorrhynchus provide favorable conditions for the growth of rice. It can not only increase the survival rate and growth rate of Tylorrhynchuss breeding, but also increase the utilization rate of rice fields, the output of Tylorrhynchuss breeding and the comprehensive economic benefits of rice farming.

Wherein, 1—paddy field; 2—field ridge; 3—ring-shaped ditch; 4—field ditch; 5—inlet channel; 6—inlet pipe; 7—inlet control assembly; 701—upper ring; 702—lower ring; 703—connecting plate; 704—sealing plate; 705—push rod; 706—movable rod; 707—upper clamping plate; 708—lower clamping plate; 709—adjusting nut; 710—guide groove; 711—guide rod; 712—shielding cloth; 713—guide hole; 8—intercepting net; 801—small grid dense area; 802—large grid evacuation area; 803—solid section; 804—eversion portion; 9—drainage pipe; 10—drainage control assembly; 1001—pipe cap; 1002—shielding plate; 1003—fixing lock cap; 1004—protrusion; 1005—fixing plate; 1006—fixing rod; 1007—arc—shaped block; 1008—adjusting lock cap; 1009—first fixing block; 1010—second fixing block; 1011—compression spring; 11—grid net.

DETAILED DESCRIPTION OF THE EMBODIMENTS

In order to make the objectives, technical solutions and advantages of the examples of the present disclosure clearer, the technical solutions in the examples of the present disclosure will be clearly and completely described below with reference to the examples of the present disclosure. Obviously, the described examples are part of examples of the present disclosure, not all examples.

The present disclosure specifically provides a Tylorrhynchus-rice symbiotic comprehensive planting and breeding method mainly based on tylorrhynchus proliferation. The planting and breeding method includes the following steps:

Step S1: Paddy Field Selection

The external source water of the rice fields is sufficient, the water quality is good, the irrigation and drainage are convenient, and there is no industrial sewage pollution. The size of the area is subject to convenient management. The suitable area for a single field is 4-6 Chinese acres. It is rectangular. The paddy field is flat and the height difference does not exceed 10 cm. Loam is the best, clay is the second, and sand is the worst. It has strong water and fertility retention. No leakage, pH value of 6.5 to 8.5 is appropriate.

Step S2: Field Layout

Figure 1:
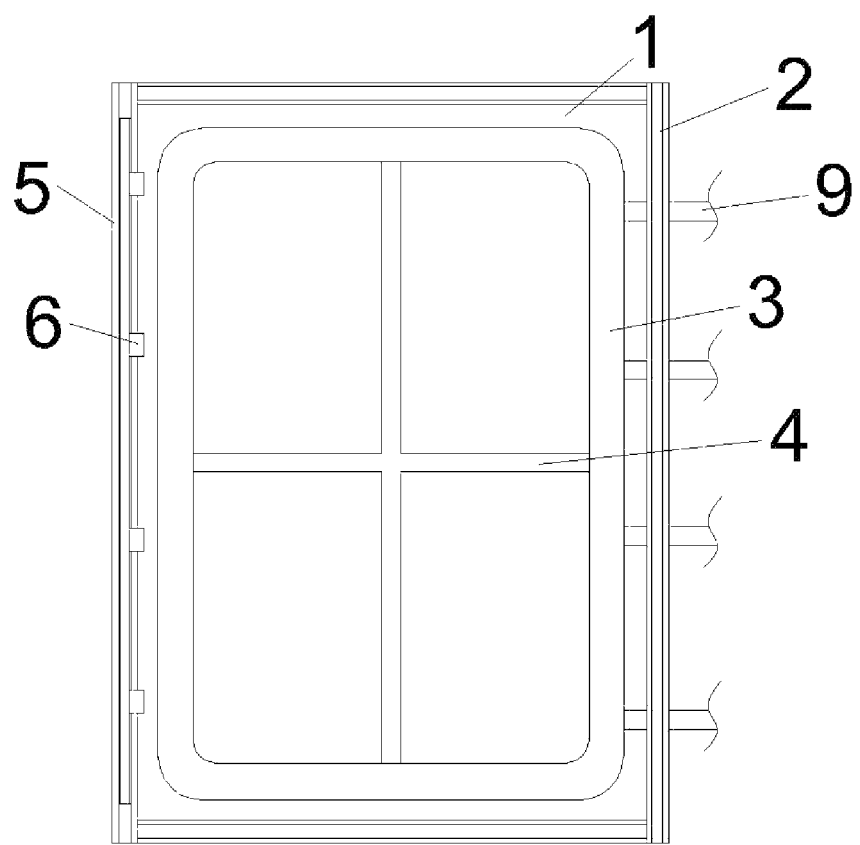
FIG. 1 is a drawing of the layout of rice fields.

Dig a ring-shaped ditch 3 along the inner side of ridge 2 around paddy field 1, 20.5 to 1 meter away from the ridge, with a width of 0.8 to 1 meter and a depth of 0.3 to 0.5 meters; for larger areas (generally more than 3 Chinese acres), dig a "cross" or "#" shaped field ditch 4 in the field. The field ditches 4 are 0.3-0.5 meters wide and 0.3-0.5 meters deep, and the sum of the ditch area accounts for no more than 8% of the paddy field area, and the ditch-ditch can be connected. Heighten and widen the ridge 2, tamped and strengthened. The height of the ridge 2 is 50-60 cm, the bottom width is 60-70 cm, and the top width is 50-60 cm. An inlet channel 5 is built on the ridge on the side of the rice field 1 and connected to the water inlet pipe 6 to the rice field; the drainage pipe 9 is built at the bottom of the ring-shaped ditch 3 on the other side of the rice field 1. The inlet pipe 6 and the drainage pipe 9 are respectively provided with an inlet control assembly 7 and a drainage control assembly 10, and are installed at the outlet and the outlet of the inlet pipe 6. A plurality of grid nets 11 (specifically shown in FIG. 1) are provided at the drain outlet of the drainage pipe 9 and the net diameters of the grid nets 11 are sequentially reduced.

Step S3: Soil Preparation and Fertilization

Paddy field 1 should be applied with sufficient base fertilizer, and the amount of fertilizer should be controlled at 1000-2000 kg/Chinese acre according to the fertility of the land. After evenly spreading into the field, irrigate and prepare the land.

Step S4: Stocking of Tylorrhynchus;

From February to April or from July to August every year, after the rice field is leveled and the base fertilizer is applied, release Tylorrhynchus 7 to 15 days before transplanting; The larvae are sown in dry fields, and the mud is evenly sown in the rice fields, and the stocking density is 250-300/m$^2$.

Step S5: Management of Tylorrhynchus Proliferation;

After the feed is crushed and fermented, fully mix with 10 times the dry rice stalk powder and feed evenly; once a week, a feeding amount is 3% of the weight of the Tylorrhynchus, reduce the feeding amount on cloudy days and low air pressure, not to feed when the water temperature is higher than 35° C. or lower than 15° C.; Intensify inspections, check the ridges for loopholes and water leakage, and remove wild fish, crabs, rice field eels and other pest predators.

Step S6: Rice Planting

Choose rice varieties with strong fertility tolerance, lodging resistance, disease resistance, moderate growth period, and good quality. Mechanical harrowing the field more than 2 times to make the mud floating and rotten, the field surface is fully leveled, and the height difference of the field surface is not more than 3 cm. Seedling transplanting can be mechanical transplanting or throwing seedlings, and the seedlings should be shallow, even, stable and straight. Planting about 100,000 basic seedlings per Chinese acre can appropriately increase the planting density on the inner side of the ridge and beside the ditch, and give full play to the marginal advantages.

Step S7: Field Management

Manage according to standard rice planting procedures. Fertilization is mainly based on basic fertilizer, supplemented by topdressing, mainly organic fertilizer, supplemented by chemical fertilizers, topdressing is little amount and multiple times, select good quality cold commercial organic fertilizers, and the use of urea and other chemical fertilizers harmful to Tylorrhynchus is strictly prohibited; prevention should be primary control of diseases, pests and weeds in paddy field, comprehensive prevention and control, and reduce the amount of pesticide application. High-efficiency, low-toxicity, and low-residue biological pesticides are the best choice for rice disease control. Organophosphorus and pyrethroid pesticides that are highly sensitive to Tylorrhynchus are prohibited. To ensure the safety of Tylorrhynchus, it is necessary to strictly control the safe use concentration of pesticides. Spray the pesticides on the rice leaves instead of spraying into the water. It is advisable to apply the pesticides separately. Add water to the rice field to 15-20 cm before spraying, and change the water in time after spraying.

Step S8: Water Level Controlling

The water level for rice transplanting is 2 to 3 cm; After transplanting seedlings, water shall be injected immediately to keep them green, and the water level shall be controlled at 4 6 cm. After the seedlings return to green, the water level of the paddy field shall be naturally dried to 3 cm to promote tillering; When the total number of stems and tillers reaches 80% of the expected number of panicles, stop watering and dry the field up naturally. According to the growth of seedlings and leaf color, dry the field until there is slight crack on the field surface. After drying the field, water 5 cm from booting period, keep water layer 10 ~ 15 cm at heading and flowering period, dry and wet in the middle and late period of grain filling; Drain the accumulated water in the field 7 days before rice harvest and keep the field moist.

Step S9: Rice Harvesting;

Manual harvesting or mechanical harvesting, but note that the turning angle of the harvester should not be too large, so as not to affect the leveling of the field and the Tylorrhynchus in the field. Fill water in time after harvesting and keep the water level 5-10 cm.

Step S10: Tylorrhynchus Capturing.

When the Tylorrhynchuss are sexually mature, dry the rice field for 1 to 2 days, in the dark night, water 20 to 30 cm, after a large number of sexually mature Tylorrhynchuss float, open the drainage pipe and arrange a soft gauze net at the drain to catch the Tylorrhynchus, the captured Tylorrhynchus are placed in a container with holes, when the Tylorrhynchus are drilled out of the holes to separate them from the debris, then clean with clean water at 14° C.-18° C. for 2 to 3 times, and temporarily store at 13° C.-15° C.

In the above step S3, organic fertilizers such as manure and cake fertilizer with long fertilizer efficiency are preferred for the base fertilizer.

In the above step S4, the Tylorrhynchus larvae of 50 to 60 rigid nodes or more are selected Tylorrhynchus, and the larvae have no damage, no disease, and good vigor.

In the above step S5, coarse feed such as soybean meal, corn flour, wheat bran, and bran may be selected as the feed.

In the above step S6, the rice variety is Guang 8 You 165 or Guang 8 You 169 or Guang 8 You 2168 or Guang 8 You Jin Zhan or Wufeng You 615 or Meixiang Zhan 2.

In the above step S8, the rice field where Tylorrhynchuss and rice grow in symbiosis should be lightly sun-dried to prevent the Tylorrhynchus from dehydration and death during the sun-dried field.

In the above step S9, most of the straw is returned to the field after being crushed.

In the above step S10, the water flow speed should be well controlled during the capturing process, and the flow speed should adopt a slow-fast-slow rhythm to facilitate the Tylorrhynchus capturing.

Figure 2:
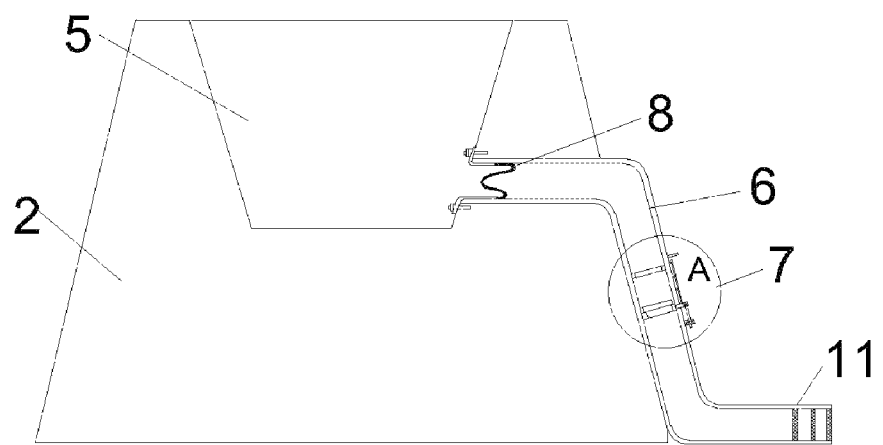
FIG. 2 is a drawing of the water inlet pipe setting.
Figure 3:
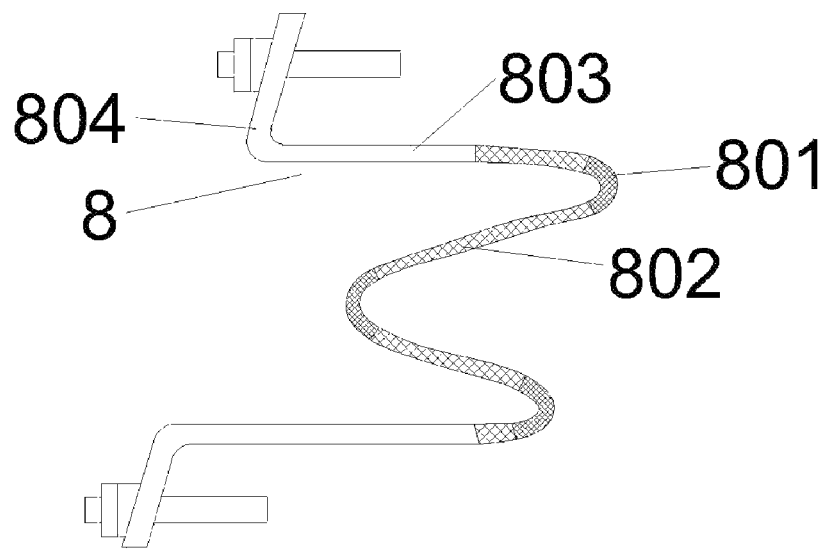
FIG. 3 is an enlarged view of the interception net in FIG. 2.
Figure 4:
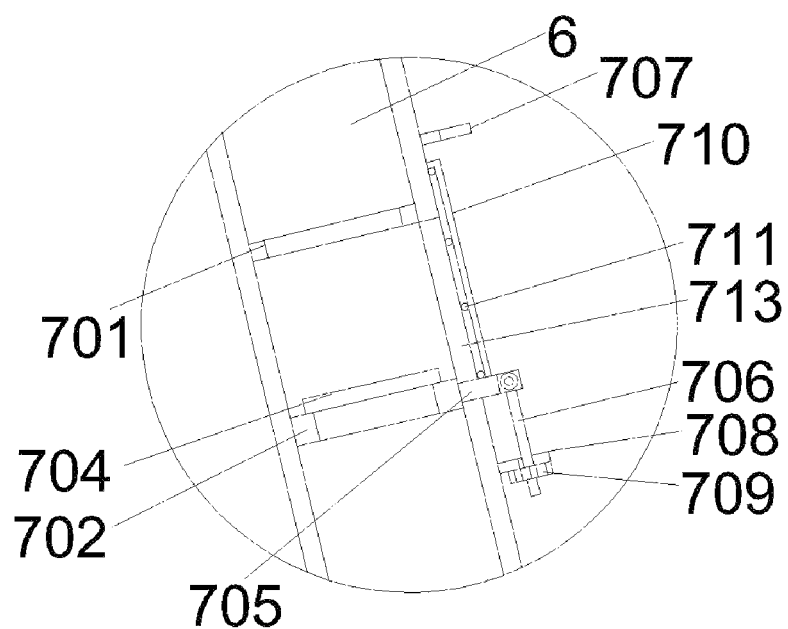
FIG. 4 is an enlarged view of A in FIG. 2.
Figure 5:
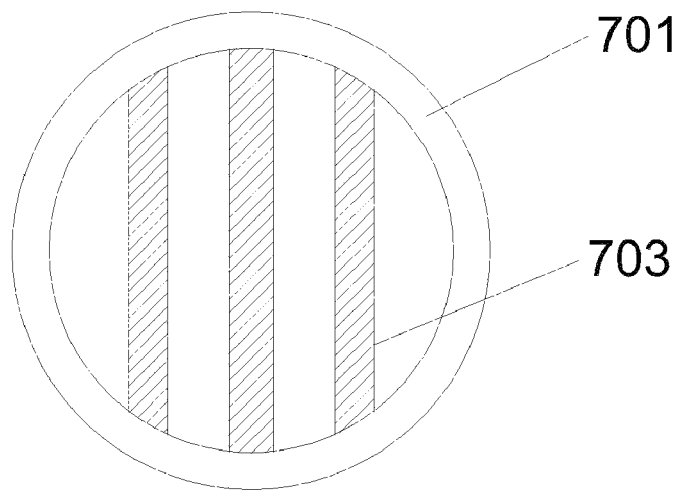
FIG. 5 is a structural diagram of the upper ring.
Figure 6:
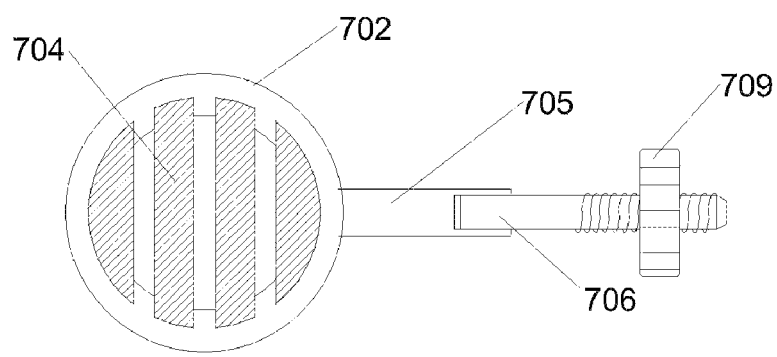
FIG. 6 is a structural diagram of the lower ring.
Figure 7:
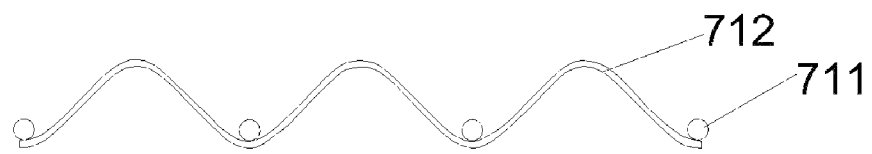
FIG. 7 is a connection diagram of the shielding portion and the guide rod.
Figure 8:
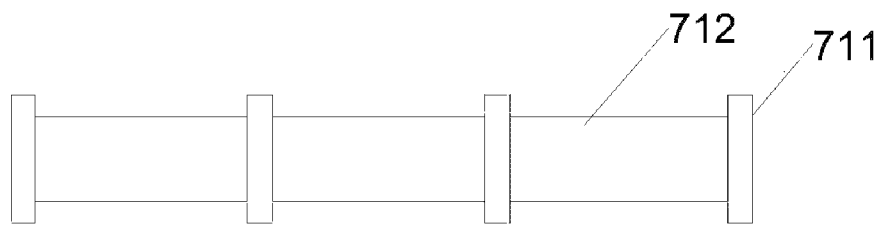
FIG. 8 is a top view of FIG. 7.

In the present disclosure, as shown in FIGS. 2 and 3, an interception net 8 is installed at the inlet of the water inlet pipe 6, and the side section of the interception net 8 is "W"-shaped structure, the interception net includes a solid section 803 extending along the inner wall of the water inlet pipe 6. The distal end of the solid section 803 is provided with a large grid evacuation area 802 and a small grid dense area 801 that are connected in series at intervals, and the small grid dense area 801 is distributed at the bending apex of the interception net 8, the proximal end of the solid section 803 is provided with an eversion portion 804 which is attached to the side wall of the water inlet channel 5 and is fixedly connected by a screw.

After the temporary water in the water inlet channel 5 enters the water inlet pipe 6, the water flow direction is along the horizontal direction of the water inlet pipe 6. The interception net 8 is designed as a "W"-shaped cross-section structure, and the bent top of the "W" structure is designed as a small grid dense area 801, and between the bent top is designed as a large grid evacuation area 802 In this way, when the temporary water in the inlet channel 5 enters the inlet pipe 6, the water flow first touches the top of the inward bent in the middle of the interception net 8, but because the top of the inward bent is designed as a small grid dense area 801, large particles debris and predators move along the "W"-shaped net surface on both sides of the top of the inward bent, passing through the large grid evacuation area 802, but because the grid of the large grid evacuation area 802 generally only allows slightly larger sand or pebbles to pass through, the predators cannot pass through the grid. Therefore, the predators gather along the top of the large grid evacuation area 802, but because the top of the bend is a small grid dense area 801, coupled with the impact of water flow on the axis, the water flow forms a vortex shape in the interception net 8, and most of the water flows through the large grid evacuation area 802, thereby ensuring the normal flow rate of the water flow, and at the same time, intercepting the predators in the inlet channel 5, to increase the reproduction speed of the Tylorrhynchus.

As shown in FIGS. 4-8, the water inlet control assembly 7 includes an upper ring 701 and a lower ring 702 installed in the inner cavity of the water inlet pipe 6. The inner diameter of the lower ring 702 is smaller than the inner diameter of the upper ring 701, so the upper ring 701 is fixedly installed in the inner cavity of the water inlet pipe 6, and the inner ring of the upper ring 701 is provided with evenly spaced connecting plates 703, and the lower ring 702 can slide along the inner cavity of the water inlet pipe 6, so the proximal surface of the lower ring 702 is provided with a sealing plate 704 that interacting distributed the connecting plate 703. When the lower ring 702 moves up below the upper ring 701, the sealing plate 704 and the connecting plate 703 are spaced apart to form a solid plate, blocking the water in the water inlet channel 5 from passing through the water inlet pipe 6.

A push rod 705 is provided on the side wall of the lower ring 702, and the free end of the push rod 705 extends from a guide hole 713 on the wall of the water inlet pipe 6 to the outside of the water inlet pipe 6, and the guide hole 713 is arranged between the upper ring 701 and the lower ring 702, the free end of the push rod 705 is movably connected with a movable rod 706, the end of the movable rod 706 is threadedly connected with an adjusting nut 709, and the upper and lower ends of the guide hole 713 are respectively provided with an upper clamping plate 707 and a lower clamping plate 708, the ends of the upper clamping plate 707 and the lower clamping plate 708 are each provided with a mounting groove recessed toward the wall of the water inlet pipe 6.

Two sides of the guide hole 713 are respectively provided with guide grooves 710, and a plurality of guide rods 711 are arranged between the two guide grooves 710. Wherein, the guide rods 711 at both ends of the guide groove 710 are fixedly connected to the guide groove 710. A shielding cloth 712 is arranged under the guide rod 711. When the shielding cloth 712 is unfolded, it is closely attached to the outer end of the guide hole 713 to prevent the water in the water inlet pipe 6 from overflowing the pipe wall.

When it is necessary to supply water to the field, rotate the adjusting nut 709, move the movable rod 706 out of the mounting groove of the upper clamping plate 707, push the push rod 705, and move the push rod 705 down to the lower end of the guide hole 713. During this process, the shielding cloth 712 switches from bending to flattening, tightly abuts the outer wall of the water inlet pipe 6, completely shields the guide hole 713, and prevents the water in the water inlet pipe 6 from overflowing the pipe wall. Then, rotate the movable rod 706, the movable rod 706 is clamped in the mounting groove on the lower clamping plate 708, and rotate the adjusting nut 709 to fix. The whole structure is reasonable in design, easy to operate, and has strong practicability.

Figure 9:
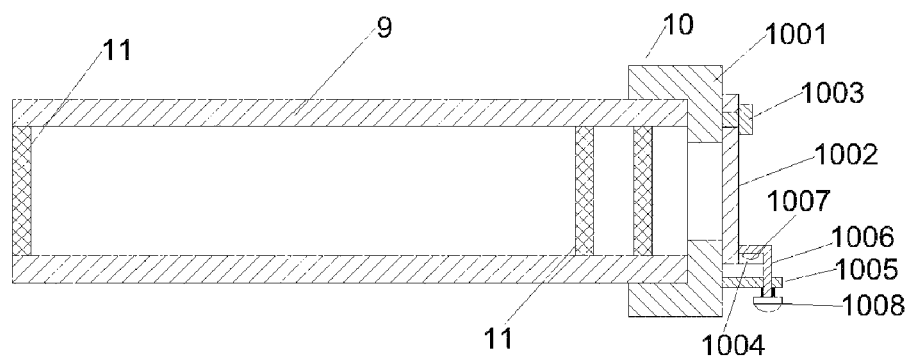
FIG. 9 is a structure drawing of the drainage pipe.
Figure 10:
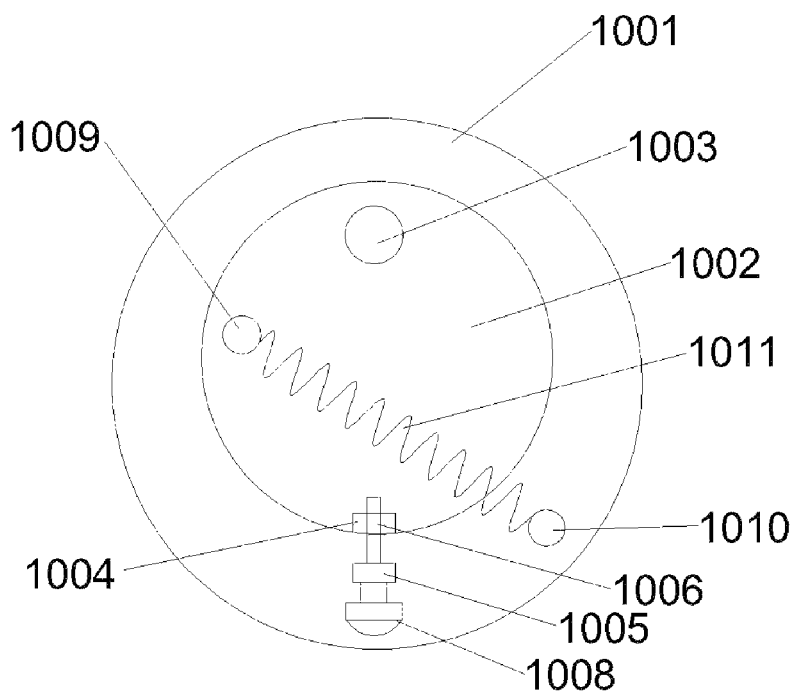
FIG. 10 is a side view of the cap.
Figure 11:
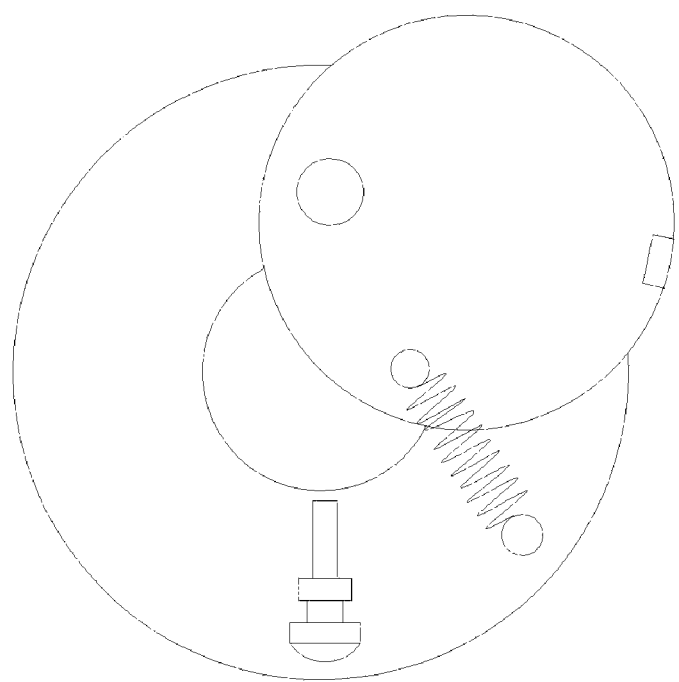
FIG. 11 is a structural drawing of the shielding plate after it has been rotated.

As shown in FIGS. 9-11, the drainage control assembly 10 includes a pipe cap 1001, the pipe cap 1001 is sleeved at the drainage outlet of the drainage pipe 9, and the pipe cap 1001 is provided with an inner cavity of the drainage pipe 9, the inner diameter of the drain hole is smaller than the inner diameter of the drain pipe 9. The outer wall of the pipe cap 1001 is provided with a shielding plate 1002, and the shielding plate 1002 is connected to the outer wall of the pipe cap 1001 through a fixing lock cap 1003, and the shielding plate 1002 can rotate around the fixing lock cap 1003, the bottom of the outer wall of the shielding plate 1002 is provided with a protrusion 1004, the bottom of the outer wall of the pipe cap 1001 is provided with a fixing plate 1005 coaxial with the protrusion 1004, the protrusion 1004 and the fixing plates 1005 are connected by a fixing rod 1006.

Wherein, the lower end of the fixing rod 1006 is threadedly connected with an adjusting lock cap 1008, and its upper end is bent along the upper end surface of the protrusion 1004 to form a horizontal section. The lower end surface of the horizontal section is provided with an arc-shaped block 1007. The arc-shaped block 1007 is embeddable in the groove on the protrusion 1004, so as to realize the shielding plate 1002 to shield the drainage hole.

In order to facilitate the use of the shielding plate 1002, a first fixing block 1009 is provided on the outer wall of the shielding plate 1002, a second fixing block 1010 is provided on the outer wall of the pipe cap 1001, the first fixing block 1009 and the second fixing block 1010 are connected by a compression spring 1011. When the shielding plate 1002 is in the closed state, the compression spring 1011 is in a stretched state, and there is traction force between the first fixing block 1009 and the second fixing block 1010. When the shielding plate 1002 needs to be opened, due to the traction force of the compression spring 1011 between the second fixing block 1010 and the first fixing block 1009. In the process of rotating the shielding plate 1002, the compression spring 1011 recovers its deformation, which reduces the resistance to the rotation of the shielding plate 1002 and makes the shielding plate 1002 rotate better. At the same time, due to the existence of the compression spring 1011 after rotation, the shielding plate 1002 can be effectively prevented from closing automatically.

The technical solution of the present disclosure will be clearly and completely described below with reference to the examples.

Example 1

Choose a rectangular rice field with sufficient water source, good water quality, and industrial pollution-free, with an area of 5.5 Chinese acre, the rice field is flat, loamy, and pH 7.5. Do a good job in field engineering, apply enough base fertilizer, and apply 1500 kg/Chinese acre. After irrigation and soil preparation, sow larvae in dry fields, and larvae of more than 50 knots are released 15 days before transplanting, and the stocking density is 250/m2. Fermented feed is fed once a week, and the amount of each feeding is 3% of the body weight of the Tylorrhynchus. Intensify inspections to remove predators such as wild fish, crabs, and rice field eels. Choose planting Guang 8 You 165 rice variety, plant 80,000 basic seedlings per Chinese acre, and manage them according to standard rice planting procedures. Drain the accumulated water in the field 7 days before the rice harvest, and keep the field moist. The rice is harvested mechanically, and water is injected in time after harvesting to keep the water level 10 cm. When the Tylorrhynchus are sexually mature, the rice field is dried for 2 days. In the dark night, 30 cm of water enters. When a large number of sexually mature Tylorrhynchus float, open the drainage gate, and arrange a soft gauze net at the gate to catch the Tylorrhynchus. The captured Tylorrhynchuss are placed in a container with holes, and after the Tylorrhynchus are drilled out of the holes to achieve separation from the sundries, wash twice with clean water at 18° C. and stored temporarily at 15° C.

Example 2

Choose a rectangular rice field with sufficient water source, good water quality, and industrial pollution-free, covering an area of 4.8 Chinese acres, the rice field is flat, loamy, and pH 7.0. Do a good job in field engineering, apply enough base fertilizer, and apply 1200 kg/Chinese acre. After irrigation and soil preparation, sow larvae in dry fields, and the larvae of Tylorrhynchus above 60 knots are released 15 days before transplanting, and the stocking density was 280/m². Fermented feed is fed once a week, and the amount of each feeding is 3% of the body weight of the Tylorrhynchus. Intensify inspections to remove predators such as wild fish, crabs, and rice field eels. Choose planting Guang 8 You 169 rice variety, plant 80,000 basic seedlings per Chinese acre, and manage them according to standard rice planting procedures. Drain the accumulated water in the field 7 days before the rice harvest, and keep the field moist. The rice is harvested mechanically, and water is injected in time after harvesting to keep the water level 8 cm. When the Tylorrhynchus are sexually mature, the rice fields are dried for 2 days. In the dark night, 25 cm of water enters, when a large number of sexually mature Tylorrhynchus float, open the drainage gate and arrange a soft gauze net at the gate to catch the Tylorrhynchuss. The captured Tylorrhynchus are placed in a container with holes, and after the Tylorrhynchuss are drilled out of the holes to achieve separation from the sundries, then wash twice with clean water at 18° C. and stored temporarily at 15° C.

Example 3

Choose a rectangular rice field with sufficient water source, good water quality, and industrial pollution-free area, covering an area of 5.2 Chinese acres, the rice field is flat, loamy, and pH 7.2. Do a good job in field engineering, apply enough base fertilizer, and apply 1300 kg/Chinese acre. After irrigation and soil preparation, sow larvae in dry fields, and the larvae with 60 knots or more are released 10 days before transplanting, and the stocking density is 300 per square meter. Fermented feed is fed once a week, and the amount of each feeding is 3% of the body weight of the Tylorrhynchus. Intensify inspections to remove predators such as wild fish, crabs, and rice field eels. Choose planting Guang 8 Youjinzhan rice variety, plant about 100,000 basic seedlings per Chinese acre, and manage them according to standard rice planting procedures. Drain the accumulated water in the field 7 days before the rice harvest, and keep the field moist. The rice is harvested mechanically, and water is injected in time after harvesting to keep the water level 10 cm. When the Tylorrhynchus are sexually mature, the rice field is dried for 2 days. In the dark night, 30 cm of water enters, when a large number of sexually mature Tylorrhynchus float, open the drainage gate, and arrange a soft gauze net at the gate to catch the Tylorrhynchuss. The captured Tylorrhynchus are placed in a container with holes, and after the Tylorrhynchus are drilled out of the holes to achieve separation from the sundries, then wash twice with clean water at 18° C. and stored temporarily at 15° C.

Through the above three sets of examples, three types of Tylorrhynchus-rice symbiotic comprehensive planting and breeding method mainly based on tylorrhynchus proliferation can be obtained. The three types of comprehensive planting and breeding technologies for rice with Tylorrhynchus proliferation as the mainstay are carried out respectively for planting and raising tests, and then comparing with common methods for breeding Tylorrhynchuss in rice fields, it is concluded that the survival rate and yield of Tylorrhynchus in the three groups of examples have been improved differently. Among them, the survival rate of Tylorrhynchuss in Example 3 is the highest and the value is the highest.

Table 1 is a comparison table of the basic parameters of Example 1-3 between the cultivation of the Tylorrhynchus and the traditional cultivation of the Tylorrhynchus.

| | Survival rate (%) | Incidence of a disease (%) | Bait cost comparison (%) | Increase of growth rate (%) |
| --- | --- | --- | --- | --- |
| Example 1 | 94.79 | 3.36 | 0.92 | 14.29 |
| Example2 | 92.85 | 2.94 | 0.89 | 12.94 |
| Example3 | 96.21 | 2.05 | 0.83 | 17.45 |
| Comparative Example 1 | 84.53 | 5.32 | 1 | 0 |

Finally, it should be noted that the above are only the preferred embodiments of the present disclosure and are not intended to limit the present disclosure. Although the present disclosure has been described in detail with reference to the foregoing embodiments, for those skilled in the art, the technical solutions described in the foregoing embodiments still can be modified, or some of the technical features may be equivalently replaced. Any modification, equivalent replacement, improvement, etc., made within the spirit and principle of the present disclosure shall be included within the protection scope of the present disclosure.

What is claimed is:

1. A Tylorrhynchus rice symbiotic integrated planting and breeding method with the main purpose of Tylorrhynchus proliferation, the Tylorrhynchus-rice symbiotic integrated planting and breeding method comprising:

selecting a paddy field with an area of 4-6 Chinese acres and a pH value of 6.5 to 8.5, the paddy field being substantially flat and having a height difference of less than 10 cm;

fielding a layout, wherein fielding the layout includes:
digging a ring-shaped ditch along an inner side of a ridge around the paddy field and 0.5 to 1 meter away from the ridge, the ditch having a ditch width of 0.8-1 m and a depth of 0.3-0.5 m;
heightening, widening and tamping the ridge, the ridge having a ridge height of 50-60 cm, a bottom width of 60-70 cm, and a top width of 50-60 cm; and
building an inlet channel on the ridge on a side of the paddy field to connect a water inlet pipe to the paddy field, building a drainage pipe at a bottom of the ring-shaped ditch on another side of the paddy field, arranging a water inlet control assembly on the water inlet pipe, arranging a drainage control assembly on the drainage pipe, and arranging a plurality of grille nets at the outlet of the water inlet pipe and the drainage hole of the drainage pipe;

preparing and fertilizing soil, in which the paddy field is applied with base fertilizer, and an amount of fertilizer is controlled at 1000-2000 kg/Chinese acre according to a fertility of a land, evenly spread into the field, irrigate and prepare the soil;

stocking of Tylorrhynchus in which from February to April or from July to August leveling the paddy field, applying the base fertilizer, and releasing Tylorrhynchus 7 to 15 days before transplanting rice seedlings;

managing of Tylorrhynchus proliferation in which crushing and fermenting feed, fully mixing the feed with 10 times a weight of dry rice stalk powder and feed evenly across the paddy field, wherein, once a week, a feeding amount is 3% of the weight of the Tylorrhynchus, the feeding amount is reduced on cloudy days and low air pressure, and no feeding occurs when water temperature is higher than 35° C. or lower than 15° C.;

planting rice including mechanically harrowing the field more than two times to make mud float, fully leveling the field surface such that a height difference of the field surface is not more than 3 cm, and, using mechanical transplanting or manually planting seedlings, planting 100,000 stand density per Chinese acre;

managing the field including;
fertilizing the field mainly with basic fertilizer and supplementing by topdressing, mainly with organic fertilizer, the supplementing being with chemical fertilizers and the topdressing being applied multiple times in a predetermined amount, the organic fertilizer being one or more cold commercial organic fertilizers and not harmful to Tylorrhynchus;
preventing and/or controlling diseases, pests and weeds in paddy field including comprehensive prevention and control, the preventing and/or controlling including strictly controlling a safe use of pesticide concentration, spraying the pesticide on the rice leaves and not into the water, and applying the pesticide in different areas of the field;
adding water to the paddy field to 15-20 cm before spraying the pesticide, and changing the water after spraying the pesticide;
controlling a water level including:
controlling the water level while transplanting the rice seedlings to be 2 to 3 cm;

after transplanting the seedlings, immediately injecting water into the seedlings to keep the seedlings green, and controlling the water level to be at about 4-6 cm;

after the seedlings return to green, drying the water level of the paddy field naturally to 3 cm to promote tillering;

when a total number of stems and tillers reaches 80% of an expected number of panicles, stop watering and drying the field up naturally;

after drying the field, watering 5 cm from a booting period, keeping the water level about 10-15 cm at a heading and flowering period; and draining the accumulated water in the field 7 days before a rice harvest and keeping the field moist;

harvesting rice including manual harvesting or mechanical harvesting, avoiding to affect a leveling of the field and the Tylorrhynchus in the field, and filling water after harvesting and keeping the water level at about 5-10 cm;

capturing Tylorrhynchus including:

when the Tylorrhynchuss are sexually mature, drying the paddy field for 1 to 2 days;

when dark at night, watering 20 to 30 cm;

after a large number of sexually mature Tylorrhynchuss float, opening the drainage pipe and arranging a soft gauze net at a drain to catch the Tylorrhynchus;

placing the captured Tylorrhynchus in a container with holes;

after drilling the Tylorrhynchus out of the holes to separate the Tylorrhynchus from debris, cleaning the Tylorrhynchus with clean water at 14° C. to 18° C. for 2 to 3 times, and temporarily storing the Tylorrhynchus at 13° C. to 15° C., wherein, a water inlet of the water inlet pipe is equipped with an interception net, and a side profile of the interception net is "W"-shaped, the interception net comprising a solid section extending along the inner wall of the water inlet pipe, and a distal end of the solid section being provided with a large grid evacuation area and a small grid dense area connected in series at intervals, the small grid dense area distributed at a bending apex of the interception net, a proximal end of the solid section being provided with an eversion part attached to a side wall of the water inlet pipe and fixedly connected by a screw.

2. The Tylorrhynchus-rice symbiotic integrated planting and breeding method according to claim 1, wherein the water inlet control assembly comprises an upper ring and a lower ring installed in the inner cavity of the water inlet pipe, the upper ring is fixedly installed in the inner cavity of the water inlet pipe, the inner ring of the upper ring is provided with evenly spaced connecting plates, the lower ring is slidable along the inner cavity of the water inlet pipe, and the proximal end surface of the lower ring is provided with a sealing plate intersecting the connecting plate, when the lower ring moves up below the upper ring, the sealing plate and the connecting plate are spaced apart to form a solid plate to block the water in the water inlet from passing through the water inlet pipe;

a push rod is provided on the side wall of the lower ring, the free end of the push rod extends from a guide hole on the wall of the water inlet pipe to the outside of the water inlet pipe, and the guide hole is arranged between the upper ring and the lower ring, the free end of the push rod is movably connected with a movable rod, the end of the movable rod is threadedly connected with an adjusting nut, the upper end of the guide hole is provided with an upper clamping plate, and the lower end of the guide hole is provided with a lower clamping plate, the ends of the upper clamping plate and the lower clamping plate are both provided with mounting grooves recessed toward the wall of the water inlet pipe.

3. The Tylorrhynchus-rice symbiotic integrated planting and breeding method according to claim 2, wherein, guide grooves are respectively provided on both sides of the guide hole, and a guide rod is provided between the two guide grooves, there are a plurality of guide rods, wherein the guide rods located at each end of the guide groove are fixedly connected with the guide groove, and a shielding cloth is arranged under the guide rods, and when the shielding cloth is unfolded, it closely adheres to the outer end of the guide hole.

4. The Tylorrhynchus-rice symbiotic integrated planting and breeding method according to claim 2, wherein the inner diameter of the lower ring is smaller than the inner diameter of the upper ring.

5. The Tylorrhynchus-rice symbiotic integrated planting and breeding method according to claim 1, wherein the drainage control assembly comprises a pipe cap, and the pipe cap is sleeved on the drainage outlet of the drainage pipe, the pipe cap is provided with a drainage hole communicating with the inner cavity of the drainage pipe, and the outer wall of the pipe cap is provided with a shielding plate which is connected to the outer wall of the pipe cap through a fixing lock cap, and the shielding plate is rotatable around a fixing lock cap, the bottom of the outer wall of the shielding plate is provided with a protrusion, the bottom of the outer wall of the pipe cap is provided with a fixing plate coaxial with the protrusion, the protrusion and the fixing plate are connected by a fixing rod.

6. The Tylorrhynchus-rice symbiotic integrated planting and breeding method according to claim 5, wherein the lower end of the fixing rod is threadedly connected with an adjusting lock cap, the upper end of the fixing rod is bent along the upper end face of the protrusion to form a horizontal section, and an lower end surface of the horizontal section is provided with an arc-shaped block, and the arc-shaped block is embeddable in the groove on the protrusion, so as to realize the shielding plate to shield the drainage hole.

7. The Tylorrhynchus-rice symbiotic integrated planting and breeding method according to claim 5, wherein the outer wall of the shielding plate is provided with a first fixing block, and the outer wall of the pipe cap is provided with a second fixing block, the first fixing block and the second fixing block are connected by a compression spring.

* * * * *